United States Patent
Hahn et al.

(10) Patent No.: US 7,985,876 B2
(45) Date of Patent: Jul. 26, 2011

(54) SUBSTITUTED DIBENZOIC ACID DERIVATIVES AND USE THEREOF

(75) Inventors: Michael Hahn, Langenfeld (DE); Eva-Maria Becker, Wuppertal (DE); Andreas Knorr, Ekrath (DE); Dirk Schneider, Wuppertal (DE); Johannes-Peter Stasch, Solingen (DE); Karl-Heinz Schlemmer, Wuppertal (DE); Frank Wunder, Wuppertal (DE); Dieter Lang, Velbert (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 12/529,713

(22) PCT Filed: Mar. 15, 2008

(86) PCT No.: PCT/EP2008/002091
§ 371 (c)(1),
(2), (4) Date: Mar. 15, 2010

(87) PCT Pub. No.: WO2008/119458
PCT Pub. Date: Oct. 9, 2008

(65) Prior Publication Data
US 2010/0168240 A1      Jul. 1, 2010

(30) Foreign Application Priority Data
Mar. 29, 2007  (DE) .......................... 10 2007 015 035

(51) Int. Cl.
C07C 63/00       (2006.01)
(52) U.S. Cl. ...................................... 562/488; 562/480
(58) Field of Classification Search ........................ None
See application file for complete search history.

(56) References Cited

U.S. PATENT DOCUMENTS

| | | |
|---|---|---|
| 6,180,656 B1 | 1/2001 | Furstner et al. |
| 6,387,940 B1 | 5/2002 | Straub et al. |
| 6,410,740 B1 | 6/2002 | Straub et al. |
| 6,414,009 B1 | 7/2002 | Straub et al. |
| 6,451,805 B1 | 9/2002 | Straub et al. |
| 6,462,068 B1 | 10/2002 | Straub et al. |
| 6,864,287 B1 | 3/2005 | Alonso-Alija et al. |
| 7,087,644 B1 | 8/2006 | Alonso-Alija et al. |
| 2004/0082798 A1 | 4/2004 | Alonso-Alija et al. |
| 2004/0176446 A1 | 9/2004 | Alonso-Alija et al. |
| 2007/0179139 A1 | 8/2007 | Alonso-Alija et al. |
| 2008/0058314 A1 | 3/2008 | Alonso-Alija et al. |

FOREIGN PATENT DOCUMENTS

| | | |
|---|---|---|
| AU | 200074150 | 4/2001 |
| EP | 0341551 A1 | 11/1989 |
| WO | WO-98/16223 A1 | 4/1998 |
| WO | WO-98/16507 A2 | 4/1998 |
| WO | WO-98/23619 A1 | 6/1998 |
| WO | 0119355 * | 2/2001 |
| WO | WO-01/19355 A2 | 3/2001 |

(Continued)

OTHER PUBLICATIONS

Ullmann's Encyclopedia of Industrial Chemistry, Copyright © 2002 by Wiley-VCH Verlag GmbH & Co. KGaA , pp. 1-51.*

(Continued)

*Primary Examiner* — Karl J Puttlitz
(74) *Attorney, Agent, or Firm* — Karen B. King; Thomas Blankinship

(57) ABSTRACT

The invention relates to novel substituted dibenzoic acid derivatives of formula (I), wherein A represents a group of formula (II) or (III), to methods for producing the same, and to their use in the treatment and/or prophylaxis of diseases. The invention also relates to the use of said substances in the production of drugs for the treatment and/or prophylaxis of diseases, especially in the treatment and/or prevention of cardiovascular diseases.

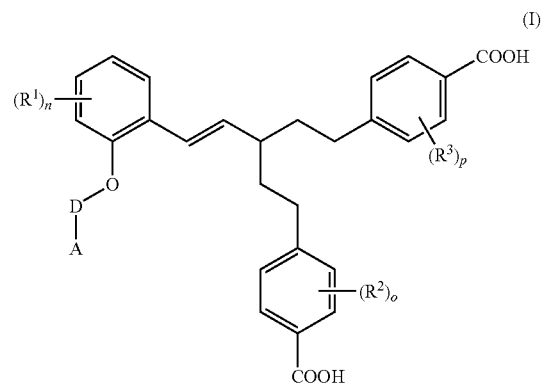

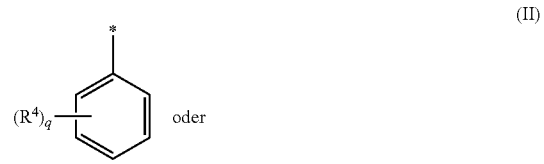

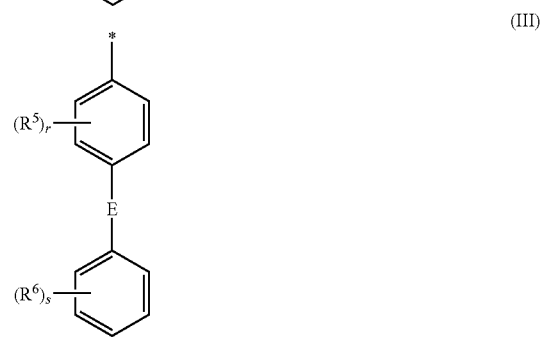

9 Claims, No Drawings

FOREIGN PATENT DOCUMENTS

| | | |
|---|---|---|
| WO | WO-01/19776 A2 | 3/2001 |
| WO | WO-01/19778 A1 | 3/2001 |
| WO | WO-01/19780 A2 | 3/2001 |
| WO | WO-02/070462 A1 | 9/2002 |
| WO | WO-02/070510 A2 | 9/2002 |

OTHER PUBLICATIONS

Fn Ko et al.: "YC-1, A Novel Activator of Platelet Guanylate Cyclase," Blood, 84, 1994, pp. 4226-4233.

A. Mulsch et al.: "Effect of YC-1, an NO-independent, Superoxide-Sensitive Stimulator of Soluble Guanylyl Cyclase, on Smooth Muscle Responsiveness to Nitrovasodilators," British Journal of Pharmacology, 120, 1997, pp. 681-689.

D. B. Glass et al.: "Stimulation of Human Platelet Guanylate Cyclase by Fatty Acids," The Journal of Biological Chemistry, vol. 252, No. 4, Feb. 25, 1977, pp. 1279-1285.

D. J. Pettibone et al.: "A Structurally Novel Stimulator of Guanylate Cyclase with Long-Lasting Hypotensive Activity in the Dog," European Journal of Pharmacology, 116, 1985, pp. 307-312.

S-M Yu et al.: "Vasorelaxant Effect of Isoliquiritigenin, a Novel Soluble Guanylate Cyclase Activator, in Rat Aorta," British Journal of Pharmacology, 114, 1995, pp. 1587-1594.

R. Gerzer et al.: "Soluble Guanylate Cyclase Purified from Bovine Lung Contains Heme and Copper," FEBS Letters, vol. 132, No. 1, Sep. 1981, pp. 71-74.

M. Hoenicka et al.: "Purified Soluble Guanylyl Cyclase Expressed in a Baculovirus/Sf9 System: Stimulation by YC-1, Nitric Oxide, and Carbon Monoxide," J. Mol. Med, 77, 1999, pp. 14-23.

L. J. Ignarro: "Regulation of Cytosolic Guanylyl Cyclase by Porphyrins and Metalloporphyrins," Advances in Pharmacology, vol. 26, 1994, pp. 35-65.

A. Mulsch et al.: "Potentiation of Vascular Responses to Non-Donors by An No-Independent Activator of Soluble Guanylyl Cyclase," Naunyn Schmiedebergs Arch. Pharmacol. 355, R47.

O. V. Evgenov et al.: "NO-Independent Stimulators and Activators of Soluble Guanylate Cyclase: Discovery and Therapeutic Potential," Nature Reviews Drug Discovery, vol. 5, Sep. 2006, pp. 755-768.

J-P Stasch et al.: "Targeting the Hem-Oxidized Nitric Oxide Receptor for Selective Vasodilatation of Diseased Blood Vessels," The Journal of Clinical Investigation, vol. 116, No. 9, Sep. 2006, pp. 2552-2561.

* cited by examiner

SUBSTITUTED DIBENZOIC ACID DERIVATIVES AND USE THEREOF

This application is a National Stage Application filed under 35 U.S.C. §371 based on International Application No. PCT/EP2008/002091, filed Mar. 15, 2008, which claims priority to German Patent Application Number 102007015035.2, filed Mar. 29, 2007, the entire contents each of which are incorporated herein by reference. The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel substituted dibenzoic acid derivatives, processes for their preparation, their use for the treatment and/or prophylaxis of diseases, and their use for producing medicaments for the treatment and/or prophylaxis of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223, WO 98/16507 and WO 98/23619).

The above-described stimulators of soluble guanylate cyclase stimulate the enzyme either directly via the heme group (carbon monoxide, nitric oxide or diphenyliodonium hexafluorophosphate) by interacting with the iron center of the heme group and a change in conformation which results therefrom and leads to an increase in the enzymic activity [Gerzer et al., FEBS Lett. 132 (1981), 71] or via a heme-dependent mechanism which is independent of NO but leads to a potentiation of the stimulating effect of NO or CO [e.g. YC-1, Hoenicka et al., J. Mol. Med. 77 (1999) 14; or the pyrazole derivatives described in WO 98/16223, WO 98/16507 and WO 98/23619].

It has not been possible to confirm the stimulating effect, asserted in the literature, of isoliquiritigenin and of fatty acids such as, for example, of arachidonic acid, prostaglandin endoperoxides and fatty acid hydroperoxides on soluble guanylate cyclase [cf., for example, Hoenicka et al., J. Mol. Med. 77 (1999), 14].

If the heme group is removed from soluble guanylate cyclase, the enzyme still shows a detectable basal catalytic activity, i.e. cGMP is still produced. The remaining basal catalytic activity of the heme-free enzyme cannot be stimulated by any of the aforementioned known stimulators. Stimulation of heme-free soluble guanylate cyclase by protoporphyrin IX has been described [Ignarro et al., Adv. Pharmacol. 26 (1994), 35]. However, protoporphyrin IX can be regarded as a mimic of the NO-heme adduct, which is why addition of protoporphyrin IX to soluble guanylate cyclase ought to lead to production of a structure of the enzyme corresponding to the heme-containing soluble guanylate cyclase which is stimulated by NO. This is also verified by the fact that the stimulating effect of protoporphyrin IX is increased by the NO-independent but heme-dependent stimulator YC-1 described above [Mülsch et al., Naunyn Schmiedebergs Arch. Pharmacol. 355, R47].

In contrast to the above-described stimulators of soluble guanylate cyclase, the compounds of the present invention are able to activate both the heme-containing and the heme-free form of soluble guanylate cyclase. Thus, with these novel activators, the enzyme is stimulated via a heme-independent pathway, which is also verified by the fact that the novel activators firstly show no synergistic effect with NO on the heme-containing enzyme, and secondly the effect of these novel activators cannot be blocked by the heme-dependent inhibitor of soluble guanylate cyclase 1H-1,2,4-oxadiazole-(4,3-a)-quinoxalin-1-one (ODQ) [Schmidt et al., J. Clin. Invest. 116 (2006), 2552; Stasch et al., Nature Rev. Drug Disc. 5 (2006), 755].

EP 0 341 551-A1 discloses alkenoic acid derivatives as leucotriene antagonists for the treatment of disorders of the circulatory and respiratory systems. WO 01/19355, WO 01/19776, WO 01/19778, WO 01/19780, WO 02/070462 and WO 02/070510 describe dicarboxylic acid and amino dicarboxylic acid derivatives as stimulators of soluble guanylate cyclase for the treatment of cardiovascular disorders. However, it has emerged that these compounds have disadvantages in relation to their pharmacokinetic properties, such as, in particular, a low bioavailability and/or an only short duration of action after oral administration.

It was therefore an object of the present invention to provide novel compounds which act as activators of soluble guanylate cyclase but do not have the aforementioned disadvantages of the prior art compounds.

This object is achieved by the compounds described in the present invention. These compounds differ structurally in comparison with the compounds of the prior art by a 3-(carboxyphenethyl)-5-phenylpent-4-en-1-ylbenzoic acid core structure.

The present invention relates specifically to compounds of the general formula (I)

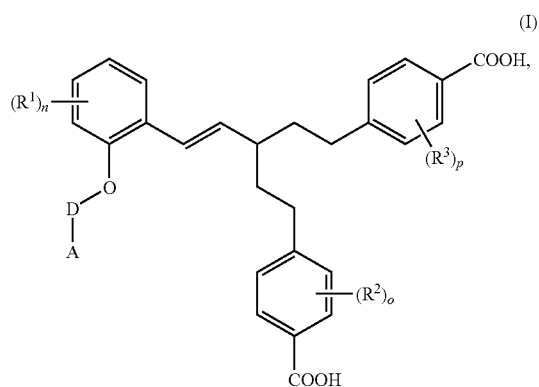

in which
A represents a group of the formula

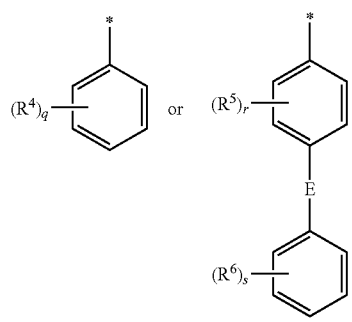

in which * represents the point of attachment to group D and

E represents a bond, —CH$_2$—, —CH$_2$—CH$_2$— or —CH═CH—,

D represents a bond or represents (C$_1$-C$_7$)-alkanediyl, (C$_2$-C$_6$)-alkanediyl-O—#, (C$_2$-C$_7$)-alkenediyl or (C$_2$-C$_7$)-alkynediyl, each of which may be mono- or polysubstituted by fluorine and in which # represents the point of attachment to group A, R$^1$, R$^2$, R$^3$, R$^4$, R$^5$ and R$^6$ independently of one another represent a substituent selected from the group consisting of halogen, (C$_1$-C$_6$)-alkyl, (C$_1$-C$_6$)-alkoxy, cyano and nitro, where alkyl and alkoxy for their part may be mono- or polysubstituted by fluorine, and n, o, p, q, r and s independently of one another each represent the number 0, 1, 2, 3 or 4, where, if R$^1$, R$^2$, R$^3$, R$^4$, R$^5$ or R$^6$ is present more than once, their meanings may in each case be identical or different, and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

(C$_1$-C$_6$)-Alkyl and (C$_1$-C$_4$)-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

$(C_1-C_7)$-Alkanediyl and $(C_7-C_6)$-alkanediyl are in the context of the invention a straight-chain or branched divalent alkyl radical having respectively 1 to 7 and 2 to 6 carbon atoms. A straight-chain alkanediyl radical having 1 to 6 or 2 to 5 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

$(C_2-C_7)$-Alkenediyl is in the context of the invention a straight-chain or branched divalent alkenyl radical having 2 to 7 carbon atoms and up to 3 double bonds. A straight-chain alkenediyl radical having 2 to 6 carbon atoms and up to 2 double bonds is preferred. Examples which may be preferably mentioned are: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

$(C_2-C_7)$-Alkynediyl is in the context of the invention a straight-chain or branched divalent alkynyl radical having 2 to 7 carbon atoms and up to 3 triple bonds. A straight-chain alkynediyl radical having 2 to 6 carbon atoms and up to 2 triple bonds is preferred. Examples which may be preferably mentioned are: ethyne-1,2-diyl, propyne-1,3-diyl, but-1-yne-1,4-diyl, but-1-yne-1,3-diyl, but-2-yne-1,4-diyl, pent-2-yne-1,5-diyl, pent-2-yne-1,4-diyl and hex-3-yne-1,6-diyl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

$(C_1-C_4)$-Alkoxycarbonyl is in the context of the invention a straight-chain or branched alkoxy radical having 1 to 4 carbon atoms which is attached via a carbonyl group. Examples which may be preferably mentioned are: methoxycarbonyl, ethoxycarbonyl, n-propoxy-carbonyl, isopropoxycarbonyl and tert-butoxycarbonyl.

Halogen in the context of the invention includes fluorine, chlorine, bromine and iodine. Chlorine, fluorine or bromine are preferred, fluorine or chlorine are particularly preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one or two substituents is very particularly preferred.

If a radical in the compounds according to the invention can be polysubstituted by fluorine, this includes in the context of the present invention a perfluoro substitution.

Preference is given in the context of the present invention to compounds of the formula (I) in which A represents a group of the formula

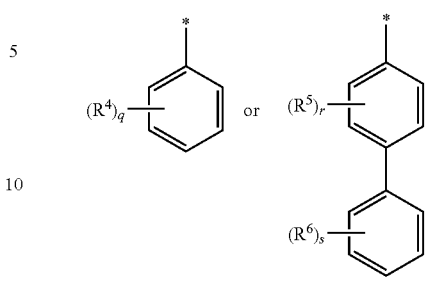

in which * represents the point of attachment to group D,
D represents a bond or $(C_1-C_7)$-alkanediyl,
$R^1$, $R^4$, $R^5$ and $R^6$ independently of one another represent a substituent selected from the group consisting of fluorine, chlorine, bromine, $(C_1-C_4)$-alkyl, trifluoromethyl, $(C_1-C_4)$-alkoxy and trifluoromethoxy,
n, q, r and s independently of one another each represent the number 0, 1 or 2,
where, if $R^1$, $R^4$, $R^5$ or $R^6$ is present more than once, their meanings may in each case be identical or different,
$R^2$ and $R^3$ each represent fluorine, and
o and p independently of one another each represent the number 0 or 1,
and the salts, solvates and solvates of the salts thereof.

Particular preference is given in the context of the present invention to compounds of the formula (I-A)

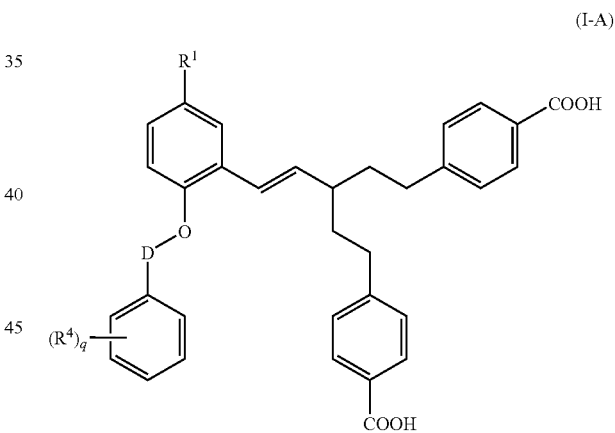

(I-A)

in which
D represents $(C_1-C_7)$-alkanediyl,
$R^1$ represents hydrogen or fluorine,
$R^4$ represents a substituent selected from the group consisting of fluorine, chlorine, methyl, tent-butyl, trifluoromethyl, methoxy and trifluoromethoxy, and
q represents the number 0, 1 or 2,
where, if the substituent $R^4$ is present twice, its meanings may be identical or different,
and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I), characterized in that compounds of the formula (II)

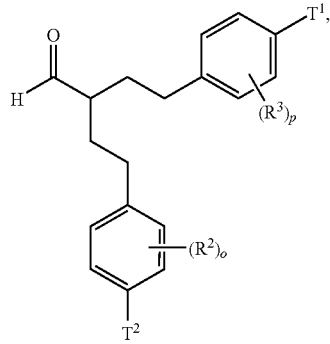
(II)

in which $R^2$, $R^3$, o and p each have the meanings given above and $T^1$ and $T^2$ are identical or different and represent $(C_1-C_4)$-alkoxycarbonyl, are either

[A] converted in an inert solvent in the presence of a base with a compound of the formula (III-A)

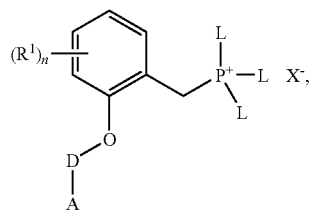
(III-A)

in which A, D, $R^1$ and n each have the meanings given above and

L represents phenyl or o-, m- or p-tolyl and

X represents halide or tosylate, into compounds of the formula (IV-A)

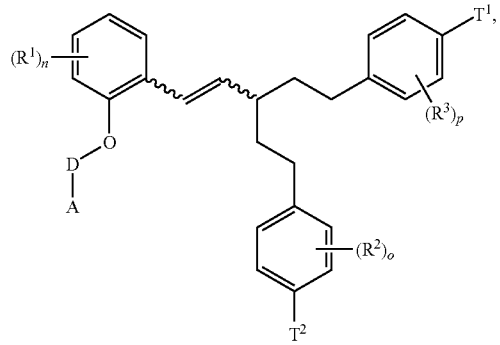
(IV-A)

in which A, D, $R^1$, $R^2$, $R^3$, n, o, p, $T^1$ and $T^2$ each have the meanings given above, or

[B] converted in an inert solvent in the presence of a base with a compound of the formula (III-B)

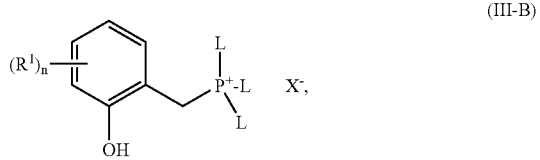
(III-B)

in which $R^1$, n, L and X each have the meanings given above, initially into compounds of the formula (IV-B)

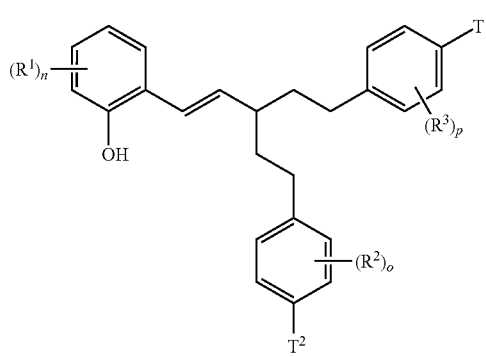
(IV-B)

in which $R^1$, $R^2$, $R^3$, n, o, p, $T^1$ and $T^2$ each have the meanings given above, and these are then coupled in an inert solvent in the presence of a base with a compound of the formula (V)

$$A\text{-}D\text{-}Q \qquad (V),$$

in which A and D have the meanings given above and

Q represents a leaving group, such as, for example, halogen, tosylate or mesylate, to give compounds of the formula (IV-C)

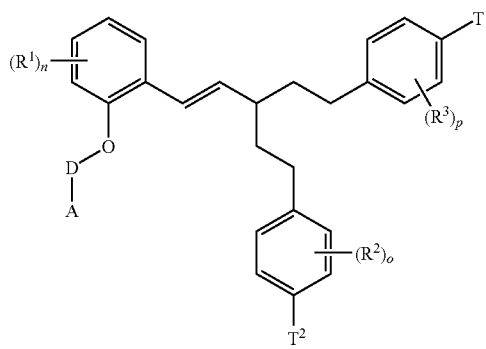
(IV-C)

in which A, D, $R^1$, $R^2$, $R^3$, n, o, p, $T^1$ and $T^2$ each have the meanings given above, and the resulting compounds of the formula (IV-A) or (IV-C) are then converted by hydrolysis of the ester groups $T^1$ and $T^2$ into the dicarboxylic acids of the formula (I)

and the compounds of the formula (I) are separated where appropriate by methods known to the skilled person into their enantiomers and/or diastereomers, and/or where appropriate reacted with the appropriate (i) solvents and/or (ii) bases or acids to give the solvates, salts and/or solvates of the salts thereof.

Examples of inert solvents for process steps (II)+(III-A)→(IV-A) and (II)+(III-B)→(IV-B) are ethers such as diethyl ether, tetrahydrofuran, glycol dimethyl ether or diethylene glycol dimethyl ether, or hydrocarbons such as benzene, toluene, xylene, pentane, hexane, heptane, cyclohexane or petroleum fractions, or mixtures of these solvents. Preference is given to using a mixture of tetrahydrofuran and hexane.

Suitable bases for these process steps are the bases customary for Wittig reactions. These include in particular strong bases such as n-, sec- or tert-butyllithium, lithium diisopropyl-amide (LDA) or lithium bis(trimethylsilyl)amide, sodium bis(trimethylsilyl)amide or potassium bis(trimethylsilyl)amide. Preference is given to n-butyllithium.

The reactions (II)+(III-A)→(IV-A) and (II)+(III-B)→(IV-B) are generally carried out in a temperature range from −78° C. to +20° C., preferably from −20° C. to +10° C.

Any cis/trans mixtures of the compound (IV-A) obtained, if appropriate, in the reaction (II)+(III-A)→(IV-A) may be separated at this stage or at the subsequent stage of the compound (I) by customary methods, for example by chromatography. The reaction (II)+(III-B)→(IV-B) is usually trans-selective.

Examples of inert solvents for process step (IV-B)+(V)→(IV-C) are ethers such as diethyl ether, dioxane, tetrahydrofuran, glycol dimethyl ether or diethylene glycol dimethyl ether, hydrocarbons such as benzene, toluene, xylene, pentane, hexane, heptane, cyclohexane or petroleum fractions, or other solvents such as acetonitrile, dimethylformamide, dimethyl sulfoxide, N,N'-dimethylpropyleneurea (DMPU) or N-methylpyrrolidone (NMP). It is also possible to employ mixtures of said solvents. Preference is given to using acetonitrile, dimethylformamide, dioxane or toluene.

Suitable bases for this process step are in particular sodium carbonate, potassium carbonate or cesium carbonate, sodium hydride or potassium hydride, lithium diisopropylamide or n-butyllithium. Preference is given to using potassium carbonate, cesium carbonate or sodium hydride.

The reaction (IV-B)+(V)→(IV-C) is generally carried out in a temperature range from +20° C. to +150° C., preferably from +50° C. to +120° C.

Hydrolysis of the ester groups $T^1$ and $T^2$ in process steps (IV-A)→(I) and (IV-C)→(I) takes place by conventional methods, by treating the esters in inert solvents with acids or bases, and with the latter converting the initially produced salts into the free carboxylic acids by treatment with acid. The ester cleavage in the case of tent-butyl esters preferably takes place with acids.

In the case of two different groups $T^1$ and $T^2$, the hydrolysis may, if appropriate, be carried out simultaneously in a one-pot reaction or in two separate reaction steps.

Inert solvents suitable for these reactions are water or the organic solvents usual for ester cleavage. These preferably include alcohols such as methanol, ethanol, n-propanol, isopropanol, n-butanol or tent-butanol, or ethers such as diethyl ether, tetrahydrofuran, dioxane or glycol dimethyl ether, or other solvents such as acetone, dichloromethane, dimethylformamide or dimethyl sulfoxide. It is also possible to employ mixtures of the solvents mentioned. In the case of a basic ester hydrolysis, preferably mixtures of water with dioxane, tetrahydrofuran, methanol and/or ethanol are employed. In the case of reaction with trifluoroacetic acid, preferably dichloromethane is used, and in the case of reaction with hydrogen chloride, preferably tetrahydrofuran, diethyl ether, dioxane or water is used.

Suitable bases are the usual inorganic bases. These preferably include alkali metal or alkaline earth metal hydroxides such as, for example, sodium hydroxide, lithium hydroxide, potassium hydroxide or barium hydroxide, or alkali metal or alkaline earth metal carbonates such as sodium carbonate, potassium carbonate or calcium carbonate. Use is particularly preferably made of sodium hydroxide, potassium hydroxide or lithium hydroxide.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, where appropriate with addition of water. Hydrogen chloride or trifluoroacetic acid are preferred in the case of the tent-butyl esters, and hydrochloric acid in the case of the methyl esters.

The ester cleavage generally takes place in a temperature range from 0° C. to +100° C., preferably at +20° C. to +60° C.

The reactions mentioned can be carried out under atmospheric, elevated or reduced pressure (e.g. from 0.5 to 5 bar). They are generally carried out under atmospheric pressure.

The aldehydes of the formula (II) can be prepared analogously to processes known from the literature, for example by a double alkylation of diallyl malonate with compounds of the formulae (VI) and (VII)

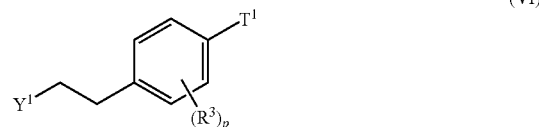

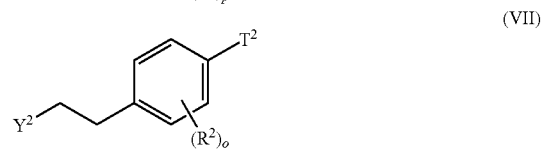

in which $R^2$, $R^3$, o, p, $T^1$ and $T^2$ each have the meanings given above and $Y^1$ and $Y^2$ are identical or different and represent a leaving group, such as, for example, halogen, mesylate or tosylate, to give compounds of the formula (VIII)

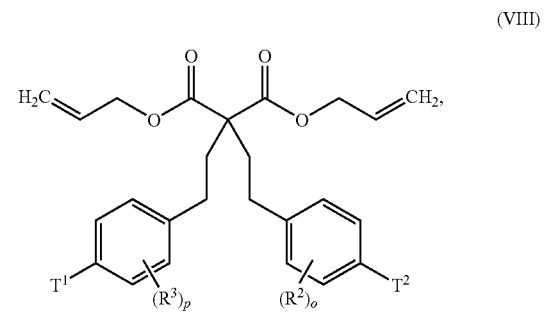

in which $R^2$, $R^3$, o, p, $T^1$ and $T^2$ each have the meanings given above, subsequent ester cleavage to give compounds of the formula (IX)

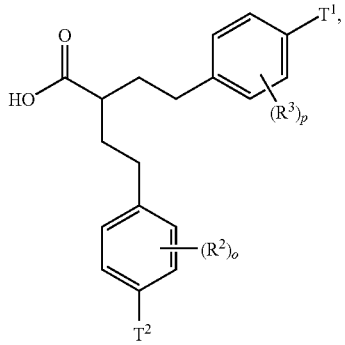

in which $R^2$, $R^3$, o, p, $T^1$ and $T^2$ each have the meanings given above,
and subsequent reduction of the carboxylic acid grouping (see also Reaction Schemes 1 and 2 below).

The compounds of the formulae (III-A) and (III-B) can be obtained by processes customary in the literature by reacting compounds of the formula (X-A) or (X-B)

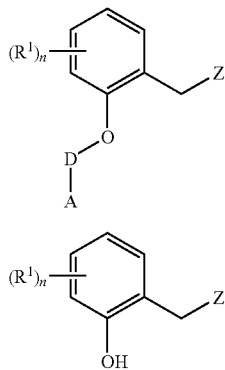

in which A, D, $R^1$ and n each have the meanings given above and

Z represents a leaving group, such as, for example, halogen or tosylate, or represents hydroxyl, for example with triphenylphosphine or (in the case of Z=OH) triphenylphosphine hydro-bromide (see also Reaction Scheme 3 below).

The compounds of the formulae (V), (VI), (VII), (X-A) and (X-B) are commercially available, known from the literature or can be prepared analogously to processes known from the literature. The compounds of the formula (X-A) can be obtained, for example, analogously to process step (IV-B)+(V)→(IV-C) by reacting compounds of the formula (X-B) in which Z represents hydroxyl with a compound of the formula (V) (see Reaction Scheme 3).

Separation of the compounds of the invention into the corresponding enantiomers and/or diastereomers can take place where appropriate, depending on expediency, even at the stage of the compounds (IV-A), (IV-B), (IV-C) or (IX), which are then reacted further in separated form in accordance with the abovedescribed process sequence. Such a fractionation of the stereoisomers can be carried out by conventional methods known to the skilled person; chromatographic methods or separation via diastereomeric salts are preferably used.

The preparation of the compounds of the invention can be illustrated by the following synthesis schemes:

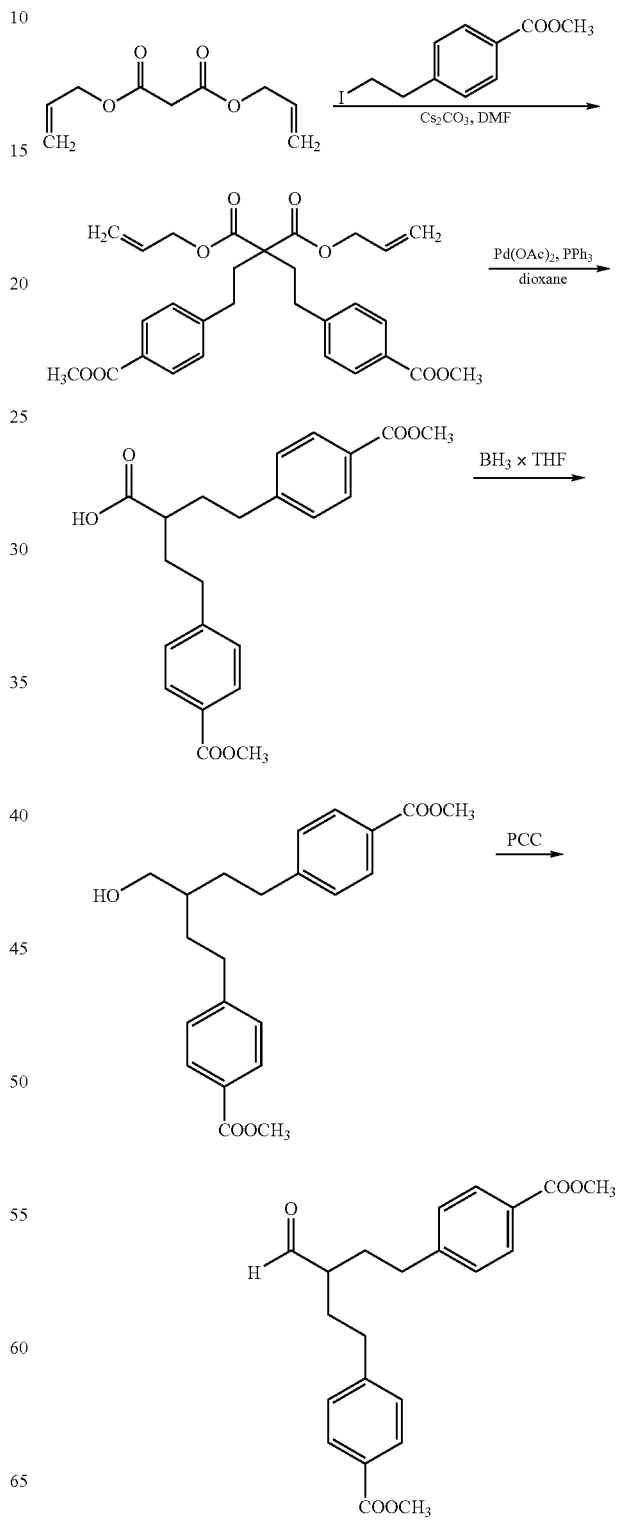

Scheme 2

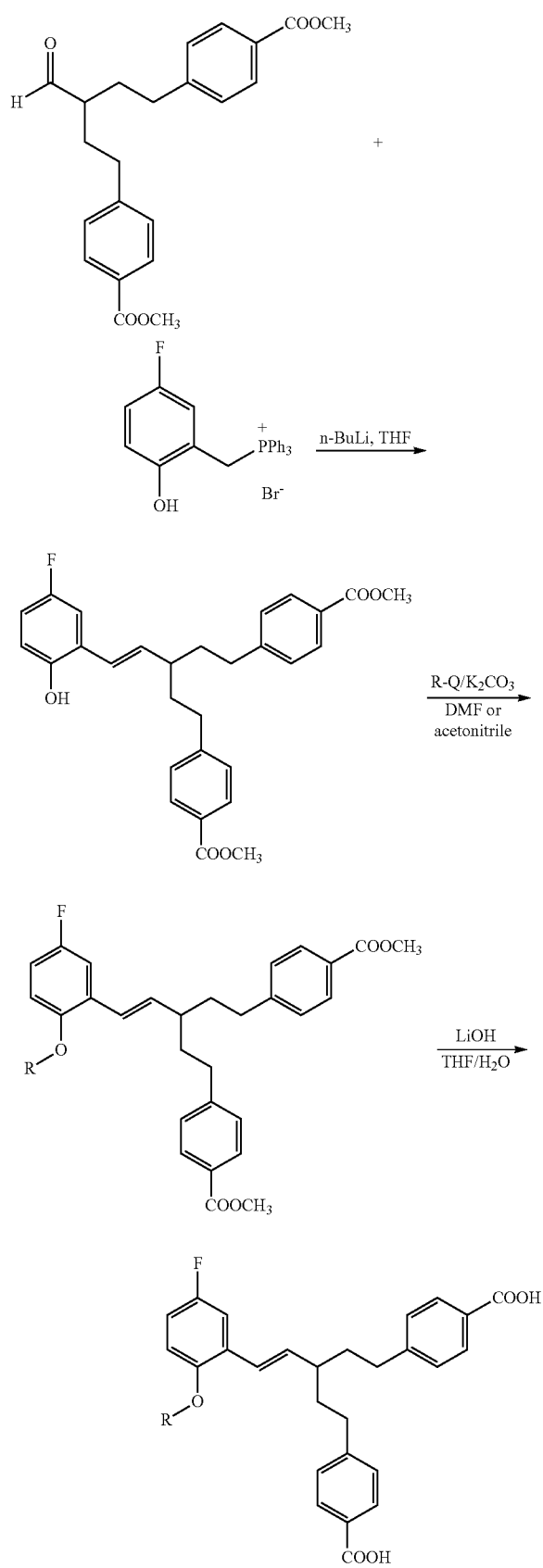

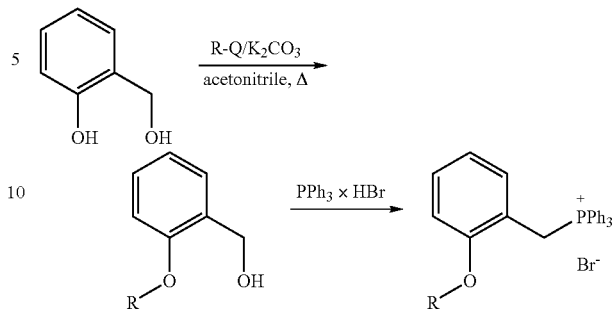

[Abbreviations: Ac = acetyl; BH₃ x THF = borane/tetrahydrofuran complex; Bu = butyl; DMF = dimethylformamide; PCC = pyridinium chlorochromate; Ph = phenyl; Q = leaving group, e.g. halogen; THF = tetrahydrofuran].

The compounds according to the invention have valuable pharmacological properties and can be used for the prevention and treatment of disorders in humans and animals.

The compounds of the present invention exhibit, as particular and surprising feature, advantageous pharmacokinetic properties such as, for example, an increased bioavailability and/or a prolonged duration of action after oral administration.

The compounds according to the invention lead to vasorelaxation, to an inhibition of platelet aggregation and to a reduction in blood pressure, and to an increase in coronary blood flow. These effects are mediated by direct activation of soluble guanylate cyclase and an intracellular increase in cGMP.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemias such as myocardial infarction, stroke, transistoric and ischemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:

organic nitrates and NO donors such as, for example, sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;

NO-independent but heme-dependent stimulators of guanylate cyclase, such as, in particular, the compounds described in WO 00/06568, WO 00/06569, WO 02/42301 and WO 03/095451;

agents having antithrombotic activity, for example and preferably from the group of platelet aggregation inhibitors, of anticoagulants or of profibrinolytic substances;

active ingredients which lower blood pressure, for example and preferably from the group of calcium antagonists, angiotensin All antagonists, ACE inhibitors, endothelin antagonists, renin inhibitors, alpha-receptor blockers, beta-receptor blockers, mineralocorticoid receptor antagonists, and of diuretics; and/or active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, BAY 59-7939, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin All antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein (a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, nontoxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral and intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations

| | |
|---|---|
| abs. | absolute |
| aq. | aqueous |
| CI | chemical ionization (in MS) |
| DCI | direct chemical ionization (in MS) |
| DMF | dimethylformamide |
| DMSO | dimethyl sulfoxide |
| ee | enantiomeric excess |
| EI | electron impact ionization (in MS) |
| eq. | equivalent(s) |
| ESI | electrospray ionization (in MS) |
| Ex. | Example |
| GC | gas chromatography |
| h | hour(s) |
| HPLC | high pressure, high performance liquid chromatography |
| LC/MS | coupled liquid chromatography-mass spectroscopy |
| min | minute(s) |
| MS | mass spectroscopy |
| NMR | nuclear magnetic resonance spectroscopy |
| $R_f$ | retention index (in TLC) |
| RT | room temperature |
| $R_t$ | retention time (in HPLC) |

| | |
|---|---|
| THF | tetrahydrofuran |
| TLC | thin-layer chromatography |
| UV | ultraviolet spectroscopy |
| v/v | volume to volume ratio (of a solution) |

LC/MS Methods:

Method 1 (LC-MS)

MS instrument type: Micromass ZQ; HPLC instrument type: HP 1100 series; UV DAD; column: Phenomenex Synergi 2μ, Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS)

MS instrument type: Micromass ZQ; HPLC instrument type: Waters Alliance 2795; column: Phenomenex Synergi 2μ, Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS)

Instrument: Micromass Platform LCZ with HPLC Agilent Series 1100; column: Phenomenex Synergi 2μ, Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS)

Instrument: Micromass Quattro LCZ with HPLC Agilent Series 1100; column: Phenomenex Synergi 2μ, Hydro-RP Mercury 20 mm×4 mm; mobile phase A: 1 l of water+0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 5 (LC-MS)

Instrument: Micromass Platform LCZ with HPLC Agilent Series 1100; column: Thermo Hypersil GOLD 3μ, 20 mm×4 mm; mobile phase A: 1 l of water+0.5 ml of 50% formic acid, mobile phase B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS)

MS instrument type: Micromass ZQ; HPLC instrument type: Waters Alliance 2795; column: Merck Chromolith SpeedROD RP-18e 100 mm×4.6 mm; mobile phase A: water+500 μl of 50% formic acid/1, mobile phase B: acetonitrile+500 μl of 50% formic acid/1; gradient: 0.0 min 10% B→7.0 min 95% B→9.0 min 95% B; flow rate: 0.0 min 1.0 ml/min→7.0 min 2.0 ml/min→9.0 min 2.0 ml/min; oven: 35° C.; UV detection: 210 nm.

Method 7 (LC-MS)

MS instrument type: Micromass ZQ; HPLC instrument type: HP 1100 Series; UV DAD; column: Phenomenex Gemini 3μ, 30 mm×3.00 mm; mobile phase A: 1 l of water+ 0.5 ml of 50% formic acid, mobile phase B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8 (LC-MS)

Instrument: Micromass Quattro LCZ with HPLC Agilent Series 1100; column: Phenomenex Onyx Monolithic C18, 100 mm×3 mm; mobile phase A: 1 l of water+0.5 ml of 50% formic acid, mobile phase B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 9 (LC-MS)

MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% formic acid, mobile phase B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

GC/MS Methods:

Method 1 (GC-MS)

Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 1.7 min).

Method 2 (GC-MS)

Instrument: Micromass GCT, GC6890; column: Restek RTX-35MS, 30 m×250 μm×0.25 μm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 8.7 min).

HPLC Methods:

Method 1 (HPLC)

Instrument: HP 1100 with DAD detection; column: Kromasil 100 RP-18, 60 mm×2.1 mm, 3.5 μm; mobile phase A: 5 ml of HClO$_4$ (70%)/1 of water, mobile phase B: acetonitrile; gradient: 0 min 2% B 0.5 min 2% B 4.5 min 90% B→9 min 90% B→9.2 min 2% B→10 min 2% B; flow rate: 0.75 ml/min; column temperature: 30° C.; UV detection: 210 nm.

Method 2 (HPLC)

Instrument: HP 1100 with DAD detection; column: Kromasil 100 RP-18, 60 mm×2.1 mm, 3.5 μm; mobile phase A: 5 ml of HClO$_4$ (70%)/1 of water, mobile phase B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Starting Compounds and Intermediates

Example 1A (5-Bromopentyl)benzene

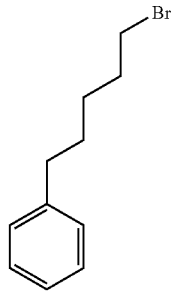

At 0° C., 50 g (0.304 mol) of 5-phenylpentan-1-ol are added to a solution of 416.7 ml (1.83 mol) of 48% strength hydrobromic acid, and the mixture is stirred at 0° C. for 30 min. The reaction solution is then stirred at 100° C. for 12 hours. After the reaction has gone to completion, the mixture is cooled to room temperature, and 200 ml of ethyl acetate are added. After extraction, the organic phase is separated off, washed with saturated sodium bicarbonate and dried over sodium sulfate. After filtration, the filtrate is evaporated to dryness. The crude product obtained is purified by flash chromatography on silica gel (mobile phase: cyclohexane). This gives 59.4 g (0.26 mol, 86% of theory) of a colorless liquid.

$^1$H-NMR (300 MHz, CDCl$_3$, δ/ppm): 7.32-7.22 (2H, m), 7.21-7.11 (3H, m), 3.40 (2H, t), 2.61 (2H, t), 1.97-1.81 (2H, m), 1.72-1.58 (2H, m), 1.56-1.39 (2H, m).

MS (CI): m/z=226 (M$^+$).

Example 2A

4-Fluoro-2-(hydroxymethyl)phenol

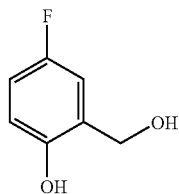

With exclusion of oxygen, 27.1 g (159.28 mmol) of methyl 5-fluoro-2-hydroxybenzoate are initially charged in 500 ml of dry THF and cooled to 0° C. With cooling, 238 ml (238 mmol) of a 1 M solution of lithium aluminum hydride in THF are then slowly added dropwise, and the mixture is then stirred at 0° C. for 1 hour and then at RT overnight. After the reaction has gone to completion, saturated ammonium chloride solution is added and the mixture is taken up in dichloromethane. The organic phase is separated off and dried over sodium sulfate. After filtration, the solvent is removed under reduced pressure. The crude product is purified chromatographically on silica gel (mobile phase: cyclohexane/ethyl acetate 20:1). This gives 18.0 g (126.6 mmol, 79% of theory) of a colorless solid.

$^1$H-NMR (400 MHz, DMSO-$d_6$, δ/ppm): 9.32 (1H, s), 7.06-7.03 (1H, m), 6.86-6.81 (1H, m), 6.74-6.71 (1H, m), 5.09 (1H, t), 4.45 (2H, d).

Example 3A (5-Fluoro-2-hydroxybenzyl)(triphenyl)phosphonium bromide

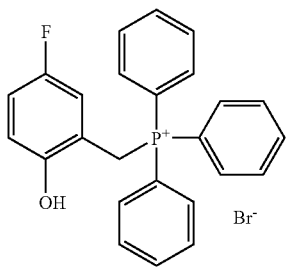

In 186 ml of acetonitrile, 18.6 g (130.87 mmol) of 4-fluoro-2-(hydroxymethyl)phenol and 42.67 g (124.32 mmol) of triphenylphosphonium hydrobromide are stirred under reflux for 3 h. After cooling, the precipitate formed is filtered off with suction and dried. This gives 58 g (124 mmol, 100% of theory) of the title compound.

$^1$H-NMR (400 MHz, DMSO-$d_6$, δ/ppm): 9.82 (1H, s), 7.95-7.84 (3H, m), 7.79-7.62 (12H, m), 7.02-6.91 (1H, m), 6.75-6.67 (1H, m), 6.66-6.58 (1H, m), 4.90 (2H, d).

Example 4A

Methyl 4-(2-iodoethyl)benzoate

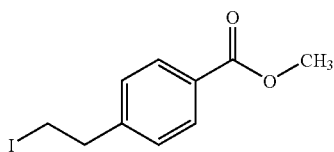

70 g (352.4 mmol) of methyl 4-(2-chloroethyl)benzoate [CAS Reg. No. 65787-72-6] and 146.2 g (880.9 mmol) of potassium iodide are suspended in 800 ml of acetonitrile and stirred under reflux for three days. After the reaction has gone to completion, the reaction solution is cooled and filtered and the filtrate is evaporated to dryness under reduced pressure. The resulting residue is purified by flash chromatography on silica gel (mobile phase:petroleum ether/ethyl acetate 30:1→20:1). This gives 101 g (348.3 mmol, 98.8% of theory) of a yellowish oil.

LC-MS (Method 7): $R_t$=2.66 min; m/z=291 (M+H)$^+$.

Example 5A

Diallyl bis{2-[4-(methoxycarbonyl)phenyl]ethyl}malonate

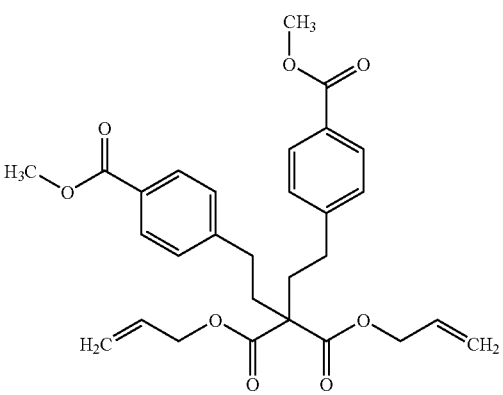

At room temperature, 61.9 g (190.02 mmol) of cesium carbonate are added to a solution of 10 g (54.3 mmol) of diallyl malonate and 47.25 g (purity 80%, 130.3 mmol) of methyl 4-(2-iodoethyl)benzoate in 100 ml DMF, and the mixture is then stirred at room temperature overnight. After the reaction has gone to completion, the reaction solution is evaporated to dryness and the residue is taken up in 100 ml of water and 100 ml of diethyl ether. The aqueous phase is extracted five times with diethyl ether and the combined organic phases are washed with saturated sodium chloride solution and dried over magnesium sulfate. After filtration, the solvent is removed under reduced pressure and the residue is purified by flash chromatography on silica gel (mobile phase: petroleum ether/ethyl acetate 10:1→5:1). This gives 22.64 g (44.52 mmol, 82% of theory) of a yellowish oil.

LC-MS (Method 7): $R_t$=3.14 min; m/z=509 (M+H)$^+$.

Example 6A

4-[4-(Methoxycarbonyl)phenyl]-2-{2-[4-(methoxycarbonyl)phenyl]ethyl}butanoic acid

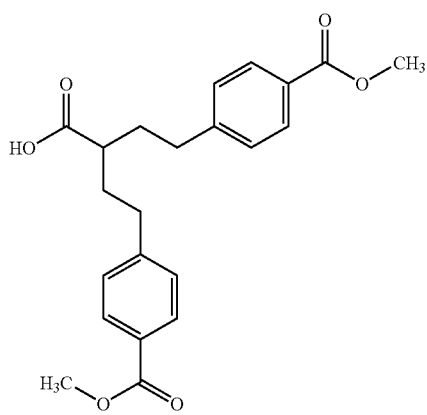

At room temperature, a solution of 20.48 ml (146.9 mmol) of triethylamine and 4.2 ml (111.29 mmol) of formic acid in 50 ml of dioxane is added to a solution of 22.64 g (44.52 mmol) of diallyl bis{2-[4-(methoxycarbonyl)phenyl]ethyl}malonate, 0.82 g (3.12 mmol) of triphenylphosphine and 200 mg of palladium acetate in 250 ml of dioxane. The reaction mixture is then stirred at 100° C. overnight. After the reaction has gone to completion, the reaction solution is cooled and the solvent is removed under reduced pressure. The residue obtained is taken up in water and ethyl acetate. The aqueous phase is extracted three times with ethyl acetate, and the combined organic phases are washed with saturated sodium chloride solution and dried over magnesium sulfate. After filtration, the solvent is removed under reduced pressure and the residue is purified by flash chromatography on silica gel (mobile phase: cyclohexane/ethyl acetate 4:1). This gives 10.4 g (27.1 mmol, 61% of theory) of a colorless solid.

$^1$H-NMR (400 MHz, DMSO-$d_6$, δ/ppm): 12.30 (1H, s), 7.86 (4H, d), 7.31 (4H, d), 3.84 (6H, s), 2.72-2.56 (4H, m), 2.29-2.18 (1H, m), 1.92-1.69 (4H, m).

LC-MS (Method 7): $R_t$=2.55 min; m/z=385 (M+H)$^+$.

Example 7A

Dimethyl 4,4'-[3-(hydroxymethyl)pentane-1,5-diyl]dibenzoate

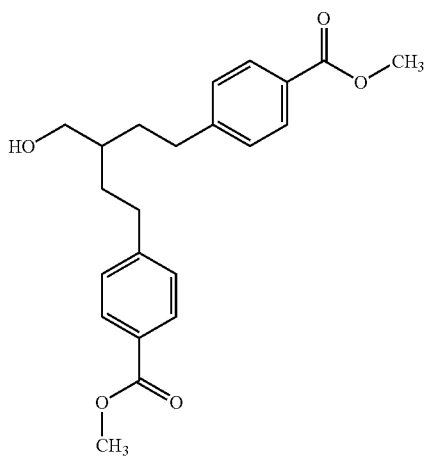

At −10° C., 54.1 ml (54.1 mmol) of a 1 M borane/THF complex solution are added dropwise to a solution of 10.4 g (27.1 mmol) of 4-[4-(methoxycarbonyl)phenyl]-2-{2-[4-(methoxy-carbonyl)phenyl]ethyl}butanoic acid in 260 ml of THF. The reaction mixture is then warmed to 0° C. and stirred at this temperature for 4 h. After the reaction has gone to completion, saturated ammonium chloride solution is added, the reaction mixture is diluted with water and ethyl acetate and the aqueous phase is extracted twice with ethyl acetate. The combined organic phases are dried over magnesium sulfate and freed from the solvent under reduced pressure. This gives 8.73 g (23.56 mmol, 87% of theory) of a colorless oil.

LC-MS (Method 7): $R_t$=2.62 min; m/z=371 (M+H)$^+$.

Example 8A

Dimethyl 4,4'-(3-formylpentane-1,5-diyl)dibenzoate

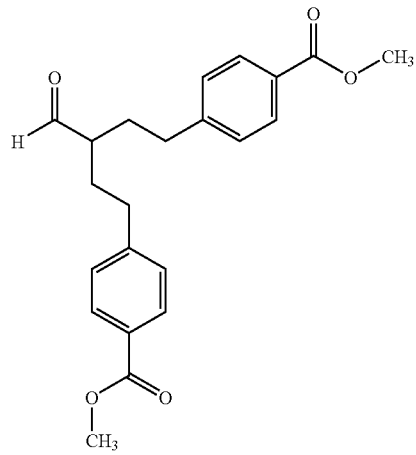

6.1 g (28.3 mmol) of pyridinium chlorochromate (PCC) are added to a solution of 8.73 g (23.6 mmol) of dimethyl 4,4'-[3-(hydroxymethyl)pentane-1,5-diyl]dibenzoate in 280 ml of dichloromethane, and the mixture is stirred at room temperature for 12 h. After the reaction has gone to completion, about 10 g of silica gel are added, and the solvent is removed to dryness under reduced pressure. The residue is purified by flash chromatography on silica gel (mobile phase: cyclohexane/ethyl acetate 4:1). This gives 7.08 g (19.22 mmol, 81.5% of theory) of a colorless oil.

LC-MS (Method 2): $R_t$=2.61 min; m/z=369 (M+H)$^+$.

Example 9A

Methyl 4-[(4E)-5-(5-fluoro-2-hydroxyphenyl)-3-{2-[4-(methoxycarbonyl)phenyl]ethyl}pent-4-en-1-yl]benzoate

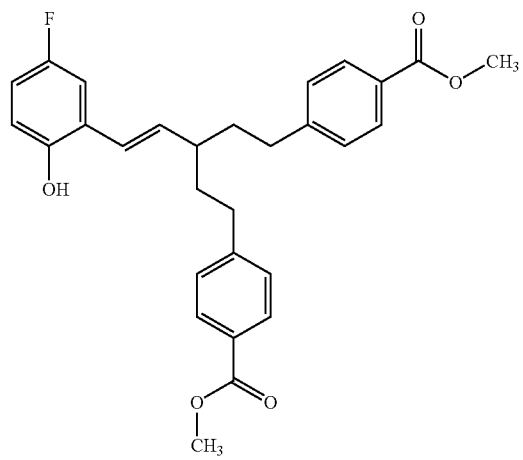

At 0° C., 2.95 ml (7.39 mmol) of a 2.5 M solution of n-butyllithium in hexane are slowly added dropwise to a solution of 1479 mg (3.2 mmol) of (5-fluoro-2-hydroxybenzyl)-(triphenyl)phosphonium bromide in 40 ml of THF. The reaction mixture is stirred at this temperature for another 45 min. At 0° C., 1080 mg (2.64 mmol) of dimethyl 4,4'-(3-formylpentane-1,5-diyl)dibenzoate in 10 ml of THF are then slowly metered in. The reaction solution is stirred at 0° C. for 5 h, saturated ammonium chloride solution is then added and the mixture is diluted with water and ethyl acetate. The organic phase is separated off, and the aqueous phase is extracted two more times with ethyl acetate. The combined organic phases are dried over sodium sulfate and filtered, and the solvent is removed to dryness. The crude product obtained is purified by flash chromatography on silica gel (mobile phase:cyclohexane/ethyl acetate 4:1). This gives 529 mg (1.11 mmol, 42% of theory) of a colorless oil.

LC-MS (Method 2): $R_t$=3.01 min; m/z=477 (M+H)$^+$.

Example 10A

Methyl 4-[(4E)-5-(2-hydroxyphenyl)-3-{2-[4-(methoxycarbonyl)phenyl]ethyl}pent-4-en-1-yl]benzoate

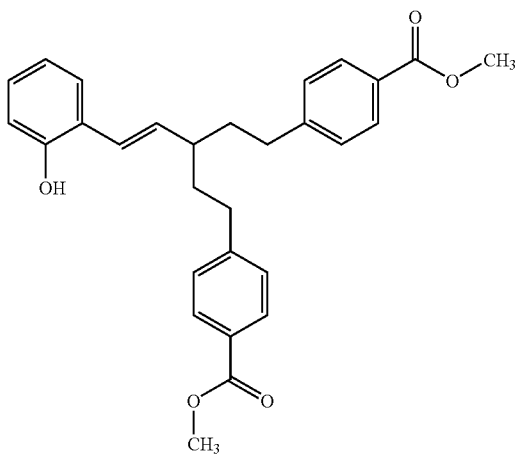

At 0° C., 2.95 ml (7.39 mmol) of a 2.5 M solution of n-butyllithium in hexane are slowly added dropwise to a solution of 1422 mg (3.2 mmol) of (2-hydroxybenzyl)(triphenyl)phosphonium bromide in 40 ml of THF. The reaction mixture is stirred at this temperature for another 45 min. At 0° C., 1080 mg (2.64 mmol) of dimethyl 4,4'-(3-formylpentane-1,5-diyl)dibenzoate in 10 ml of THF are then slowly metered in. The reaction solution is stirred at 0° C. for 5 h, saturated ammonium chloride solution is then added and the mixture is diluted with water and ethyl acetate. The organic phase is separated off, and the aqueous phase is extracted two more times with ethyl acetate. The combined organic phases are dried over sodium sulfate and filtered, and the solvent is removed to dryness. The crude product obtained is purified by flash chromatography on silica gel (mobile phase:cyclohexane/ethyl acetate 4:1). This gives 169 mg (0.37 mmol, 14% of theory) of a colorless oil.

LC-MS (Method 2): $R_t$=3.02 min; m/z=459 (M+H)$^+$.

Example 11A

Methyl 4-[(4E)-5-(5-fluoro-2-{[4-(trifluoromethyl)benzyl]oxy}phenyl)-3-{2-[4-(methoxycarbon-yl)phenyl]ethyl}pent-4-en-1-yl]benzoate

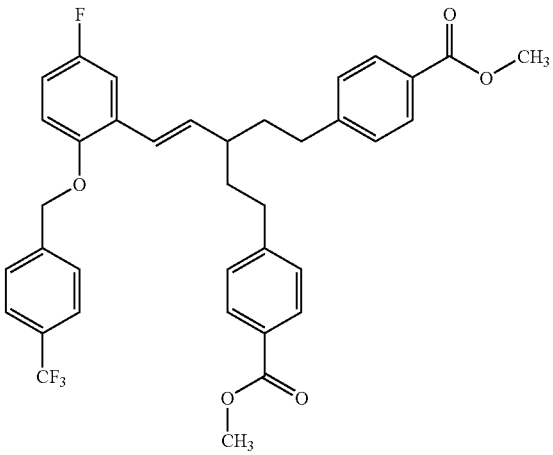

280 mg (1.2 mmol) of 1-(bromomethyl)-4-(trifluoromethyl)benzene and 162 mg (1.2 mmol) of anhydrous potassium carbonate are added to a solution of 279 mg (0.59 mmol) of methyl 4-[(4E)-5-(5-fluoro-2-hydroxyphenyl)-3-{2-[4-(methoxycarbonyl)phenyl]ethyl} pent-4-en-1-yl]benzoate in 6.5 ml of dry acetonitrile, and the mixture is then heated at 60° C. for 12 hours. The mixture is then filtered, and the filtrate is evaporated to dryness. The residue is purified by preparative HPLC. This gives 274 mg (0.43 mmol, 74% of theory) of a colorless oil.

$^1$H-NMR (400 MHz, DMSO-d$_6$, δ/ppm): 7.81 (4H, d), 7.74-7.62 (4H, m), 7.41-7.34 (1H, m), 7.29 (4H, d), 7.14-7.01 (2H, m), 6.63 (1H, d), 6.27-6.15 (1H, m), 5.24 (2H, s), 3.83 (6H, s), 2.75-2.55 (4H, m), 2.19-2.06 (1H, m), 1.85-1.73 (2H, m), 1.73-1.60 (2H, m).

LC-MS (Method 7): $R_t$=3.50 min; m/z=635 (M+H)$^+$.

EXEMPLARY EMBODIMENTS

Example 1

4-[(4E)-3-[2-(4-Carboxyphenyl)ethyl]-5-(5-fluoro-2-{[4-(trifluoromethyl)benzyl]oxy}phenyl)pent-4-en-1-yl]benzoic acid

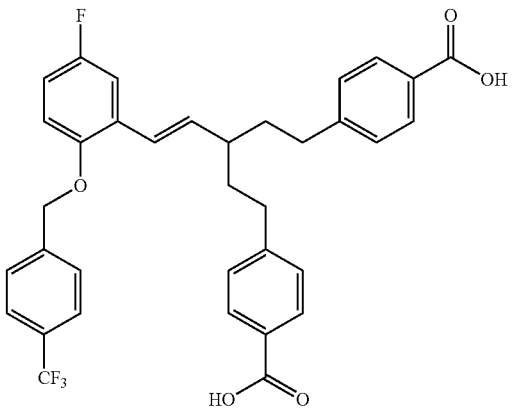

29 mg (1.23 mmol) of lithium hydroxide are added to a solution of 260 mg (0.41 mmol) of methyl 4-[(4E)-5-(5-fluoro-2-{[4-(trifluoromethyl)benzyl]oxy} phenyl)-3-{2-[4-(methoxycarbonyl)phenyl]ethyl}pent-4-en-1-yl]benzoate in 10 ml of THF and 10 ml of water, and the mixture is stirred at 50° C. for 12 hours. The mixture is then adjusted to pH 2 using 1 M hydrochloric acid and concentrated. The residue obtained is purified directly by preparative HPLC. This gives 182 mg (0.29 mmol, 72% of theory) of the title compound.

$^1$H-NMR (400 MHz, DMSO-d$_6$, δ/ppm): 12.80 (2H, broad), 7.80 (4H, d), 7.75-7.64 (4H, m), 7.41-7.35 (1H, m), 7.27 (4H, d), 7.15-7.00 (2H, m), 6.66 (1H, d), 6.28-6.18 (1H, m), 5.75 (2H, s), 2.74-2.55 (4H, m), 2.22-2.11 (1H, m), 1.85-1.72 (2H, m), 1.72-1.59 (2H, m).

LC-MS (Method 9): R$_t$=4.38 min; m/z=607 (M+H)$^+$.

The examples given in the following table are obtained in a manner analogous to the synthesis of Example 1:

| Example No. | Example Structure [Starting materials] | Analytical Data |
|---|---|---|
| 2 | 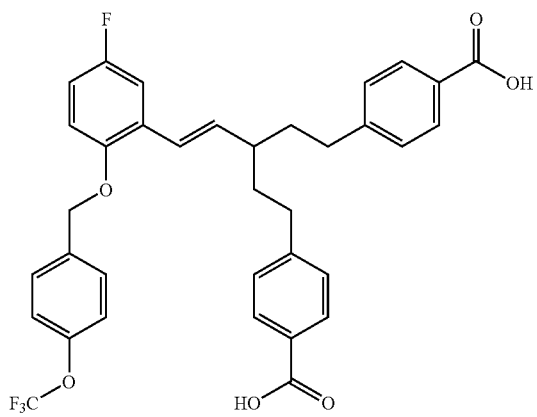<br>[starting from 1-(bromomethyl)-4-(trifluoromethoxy)benzene and Ex. 9A] | $^1$H-NMR (400 MHz, DMSO-d$_6$, δ/ppm): 12.76 (2H, broad), 7.82-7.80 (4H, d), 7.60-7.57 (2H, d), 7.39-7.33 (3H, m), 7.28-7.26 (4H, d), 7.12-7.01 (2H, m), 6.65-6.61 (1H, d), 6.25-6.18 (1H, m), 5.17 (2H, s), 2.71-2.50 (4H, m), 2.21-2.11 (1H, m), 1.82-1.74 (2H, m), 1.71-1.61 (2H, m). LC-MS (Method 8): R$_t$ = 4.41 min; m/z = 623 (M + H)$^+$. |
| 3 | 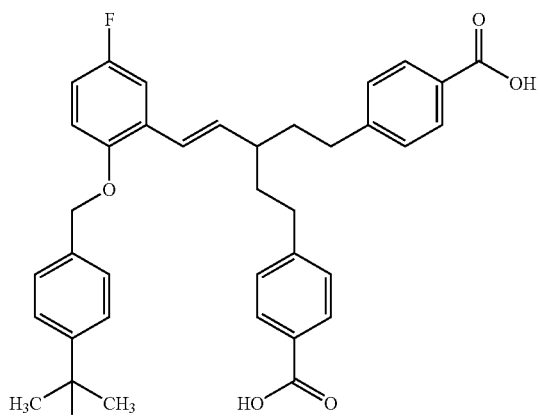<br>[starting from 4-(tert-butyl)benzyl bromide and Ex. 9A] | $^1$H-NMR (400 MHz, DMSO-d$_6$, δ/ppm): 12.77 (2H, broad), 7.83-7.80 (4H, d), 7.40-7.34 (5H, m), 7.29-7.27 (4H, d), 7.14-7.10 (1H, m), 7.06-7.01 (1H, m), 6.67-6.62 (1H, d), 6.24-6.18 (1H, m), 5.09 (2H, s), 2.71-2.49 (4H, m), 2.19-2.10 (1H, m), 1.81-1.73 (2H, m), 1.70-1.63 (2H, m), 1.24 (9H, s). LC-MS (Method 8): R$_t$ = 4.51 min; m/z = 593 (M − H)$^-$. |

| Example No. | Example Structure [Starting materials] | Analytical Data |
|---|---|---|
| 4 | 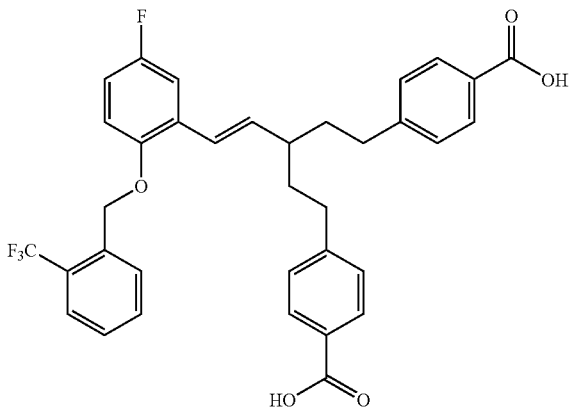<br>[starting from 1-(bromomethyl)-2-(trifluoromethyl)benzene and Ex. 9A] | $^1$H-NMR (400 MHz, DMSO-$d_6$, δ/ppm): 12.76 (2H, broad), 7.82-7.75 (6H, m), 7.71-7.67 (1H, t), 7.60-7.56 (1H, t), 7.40-7.37 (1H, m), 7.24-7.22 (4H, d), 7.13-7.03 (2H, m), 6.60-6.56 (1H, d), 6.22-6.15 (1H, m), 5.25 (2H, s), 2.71-2.50 (4H, m), 2.10-2.08 (1H, m), 1.75-1.73 (2H, m), 1.66-1.59 (2H, m).<br>LC-MS (Method 8): $R_t$ = 4.28 min; m/z = 607 (M + H)$^+$. |
| 5 | 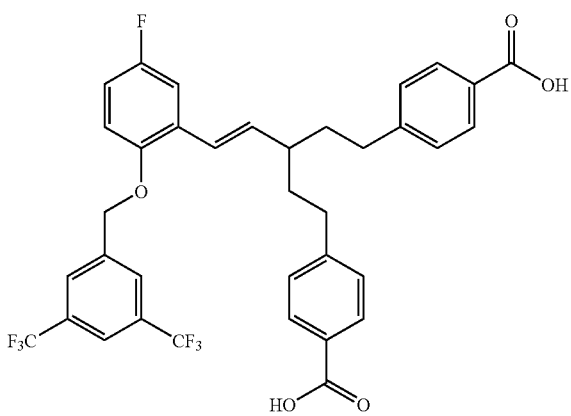<br>[starting from 1-(bromomethyl)-3,5-bis(trifluoromethyl)benzene and Ex. 9A] | $^1$H-NMR (400 MHz, DMSO-$d_6$, δ/ppm): 12.75 (2H, broad), 8.16 (2H, s), 8.06 (1H, s), 7.77-7.75 (4H, d), 7.40-7.37 (1H, m), 7.24-7.22 (4H, d), 7.15-7.05 (2H, m), 6.65-6.61 (1H, d), 6.26-6.20 (1H, m), 5.35 (2H, s), 2.68-2.49 (4H, m), 2.14-2.12 (1H, m), 1.78-1.76 (2H, m), 1.66-1.61 (2H, m).<br>LC-MS (Method 8): $R_t$ = 4.34 min; m/z = 675 (M + H)$^+$. |
| 6 | 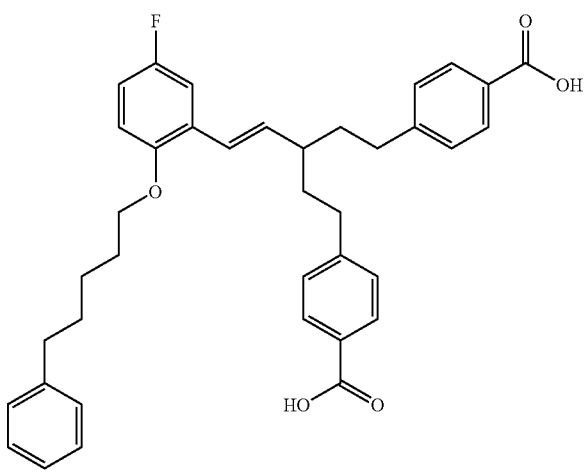<br>[starting from Ex. 1A and Ex. 9A] | $^1$H-NMR (400 MHz, DMSO-$d_6$, δ/ppm): 12.78 (2H, broad), 7.85-7.83 (4H, d), 7.34-7.29 (5H, m), 7.22-7.18 (2H, t), 7.13-7.09 (3H, m), 7.03-6.98 (2H, m), 6.60-6.55 (1H, d), 6.22-6.15 (1H, m), 3.96 (2H, t), 2.71-2.50 (6H, m), 2.14-2.12 (1H, m), 1.78-1.75 (4H, m), 1.70-1.57 (4H, m), 1.48-1.43 (2H, m).<br>LC-MS (Method 8): $R_t$ = 4.54 min; m/z = 595 (M + H)$^+$. |

| Example No. | Example Structure [Starting materials] | Analytical Data |
|---|---|---|
| 7 | 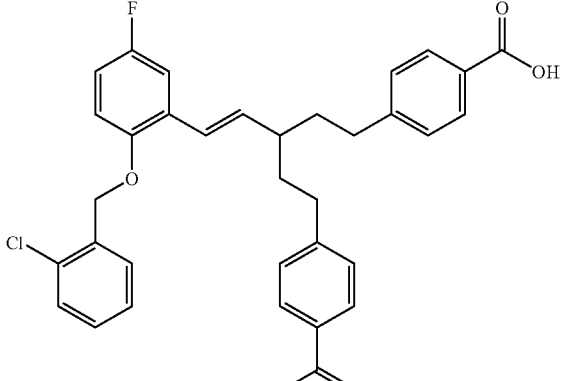<br>[starting from 2-chlorobenzyl bromide and Ex. 9A] | $^1$H-NMR (400 MHz, DMSO-$d_6$, δ/ppm): 12.77 (2H, broad), 7.80-7.78 (4H, d), 7.62-7.60 (1H, m), 7.51-7.49 (1H, m), 7.40-7.33 (3H, m), 7.26-7.24 (4H, d), 7.16-7.13 (1H, m), 7.08-7.03 (1H, m), 6.63-6.59 (1H, d), 6.23-6.17 (1H, m), 5.18 (2H, s), 2.67-2.50 (4H, m), 2.12-2.10 (1H, m), 1.76-1.75 (2H, m), 1.67-1.61 (2H, m).<br>LC-MS (Method 8): $R_t$ = 4.28 min; m/z = 571 (M − H)$^-$. |

B. Assessment of the Pharmacological Activity

The pharmacological effect of the compounds according to the invention can be shown in the following assays:

B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with 95% $O_2$/5% $CO_2$ and has the following composition: NaCl 119 mM; KCl 4.8 mM; $CaCl_2 \times 2H_2O$ 1 mM; $MgSO_4 \times 7H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the height of the contraction achieved under the influence of the test substance is compared with the height of the contraction reached in the last preceding run. The concentration necessary to reduce the contraction reached in the preceding control by 50% is calculated from this ($IC_{50}$). The standard application volume is 5 μl. The proportion of DMSO in the bath solution corresponds to 0.1%.

A representative result for the compounds according to the invention is listed in Table 1:

TABLE 1

Vasorelaxant effect in vitro

| Example No. | $IC_{50}$ [nM] |
|---|---|
| 1 | 250 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazole-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity. The result for Example 1 is shown in Table 2:

TABLE 2

Stimulation (n-fold) of recombinant soluble guanylate cyclase (sGC) in vitro by Example 1

| Concentration of Example 1 [μM] | Heme-containing sGC | | | Heme-free sGC |
|---|---|---|---|---|
| | Basal | +0.1 μM DEA/NO | +10 μM ODQ | Basal |
| 0.0 | 1.0 | 25.0 | 5.3 | 1.0 |
| 0.01 | 1.3 | 24.1 | 7.0 | 1.0 |
| 0.1 | 1.9 | 25.5 | 16.2 | 2.3 |
| 1 | 6.4 | 33.4 | 60.6 | 9.1 |
| 10 | 11.0 | 41.5 | 92.2 | 16.7 |

[DEA/NO = 2-(N,N-diethylamino)diazenolate 2-oxide; ODQ = 1H-1,2,4-oxadiazole-(4,3a)-quinoxalin-1-one].

It is evident from Table 2 that stimulation both of the heme-containing and of the heme-free enzyme is achieved. Furthermore, combination of Example 1 and 2-(N,N-diethylamino)-diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitter, (2) receiver which is linked via a multiplexer to a (3) data acquisition computer. The telemetry system makes it possible to record continuously the blood pressure and heart rate on conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 in the morning and at 19.00 in the evening.

The telemetry transmitters (TAM PA-C40, DSI) employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area on the side of the abdomen. After the abdominal cavity has been opened along the linea alba, the liquid-filled measuring catheter of the system is inserted into the descending aorta in the cranial direction above the bifurcation and fastened with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of the infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated from outside by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file bearing the experiment number which is open for this purpose.

In the standard procedure, the following are measured for 10-second periods in each case: (1) systolic blood pressure (SBP), (2) diastolic blood pressure (DBP), (3) mean arterial pressure (MAP) and (4) heart rate (HR).

Measurement acquisition is repeated under computer control at 5-minute intervals. The source data obtained as absolute value are corrected in the diagram with the currently measured barometric pressure and stored in individual data. Further technical details are given in the documentation of the manufacturing company (DSI).

The test substances are administered at 9.00 h on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 h on the day of the experiment to 9.00 h on the following day.

The data are smoothed over a presettable time by determination of the average (15-minute average, 30-minute average) and transferred as text file to a storage medium. The measurements presorted and compressed in this way are transferred into Excel templates and tabulated.

C. Exemplary Embodiments of Pharmaceutical Compositions

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

I.V.-Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

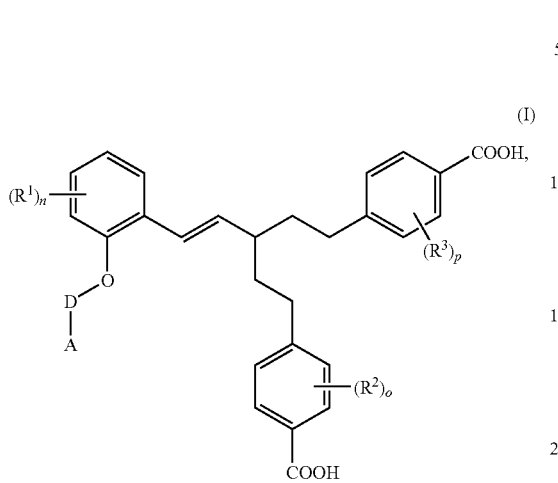

in which
A represents a group of the formula

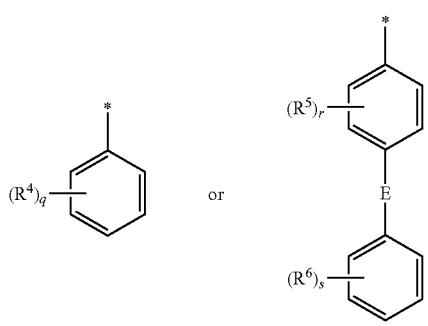

in which * represents the point of attachment to group D and

E represents a bond, —CH₂—, —CH₂—CH₂— or —CH=CH—,

D represents a bond or represents (C₁-C₇)-alkanediyl, (C₂-C₆)-alkanediyl-O—#, (C₂-C₇)-alkenediyl or (C₂-C₇)-alkynediyl, each of which may be mono- or polysubstituted by fluorine and in which # represents the point of attachment to group A, R¹, R², R³, R⁴, R⁵ and R⁶ independently of one another represent a substituent selected from the group consisting of halogen, (C₁-C₆)-alkyl, (C₁-C₆)-alkoxy, cyano and nitro, where alkyl and alkoxy for their part may be mono- or polysubstituted by fluorine, and n, o, p, q, r and s independently of one another each represent the number 0, 1, 2, 3 or 4, where, if R¹, R², R³, R⁴, R⁵ or R⁶ is present more than once, their meanings may in each case be identical or different, and salts thereof.

2. The compound of the formula (I) as claimed in claim 1, in which

A represents a group of the formula

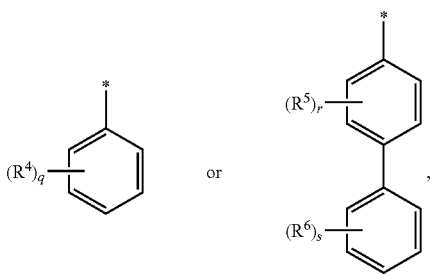

in which * represents the point of attachment to group D,

D represents a bond or (C₁-C₇)-alkanediyl,

R¹, R⁴, R⁵ and R⁶ independently of one another represent a substituent selected from the group consisting of fluorine, chlorine, bromine, (C₁-C₄)-alkyl, trifluoromethyl, (C₁-C₄)-alkoxy and trifluoromethoxy, n, q, r and s independently of one another each represent the number 0, 1 or 2, where, if R¹, R⁴, R⁵ or R⁶ is present more than once, their meanings may in each case be identical or different, R² and R³ each represent fluorine, and and p independently of one another each represent the number 0 or 1, and the salts thereof.

3. The compound as claimed in claim 1 of the formula (I-A)

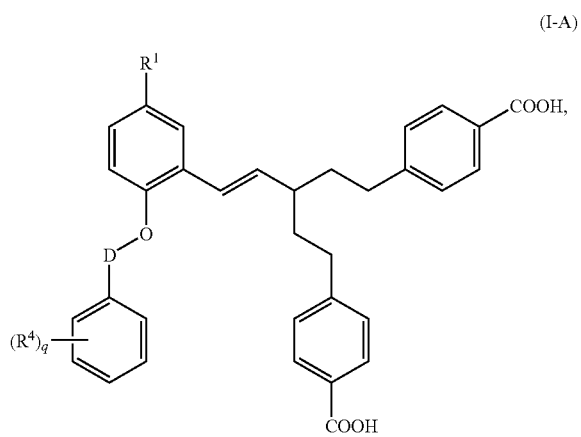

in which
D represents (C₁-C₇)-alkanediyl,
R¹ represents hydrogen or fluorine,
R⁴ represents a substituent selected from the group consisting of fluorine, chlorine, methyl, tert-butyl, trifluoromethyl, methoxy and trifluoromethoxy,
and
q represents the number 0, 1 or 2,
where, if the substituent R⁴ is present twice, its meanings may be identical or different,
and the salts thereof.

4. A process for preparing a compound of the formula (I) as defined in claim 1 wherein compounds of the formula (II)

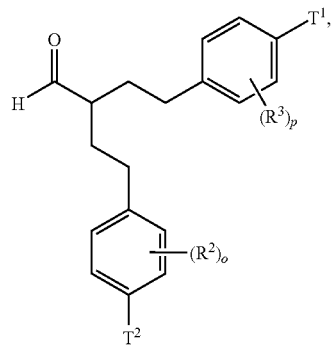

(II)

in which $R^2$, $R^3$, o and p each have the meanings given in claim 1 and $T^1$ and $T^2$ are identical or different and represent $(C_1-C_4)$-alkoxycarbonyl, are either

[A] converted in an inert solvent in the presence of a base with a compound of the formula (III-A)

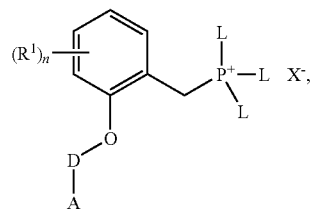

(III-A)

in which A, D, $R^1$ and n each have the meanings given in claim 1 and

L represents phenyl or o-, m- or p-tolyl and

X represents halide or tosylate, into compounds of the formula (IV-A)

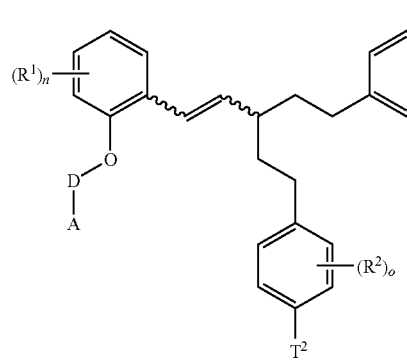

(IV-A)

in which A, D, $R^1$, $R^2$, $R^3$, n, o, p, $T^1$ and $T^2$ each have the meanings given above, or

[B] converted in an inert solvent in the presence of a base with a compound of the formula (III-B)

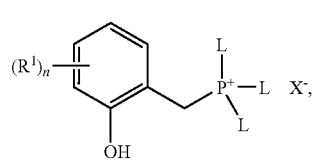

(III-B)

in which $R^1$, n, L and X each have the meanings given above, initially into compounds of the formula (IV-B)

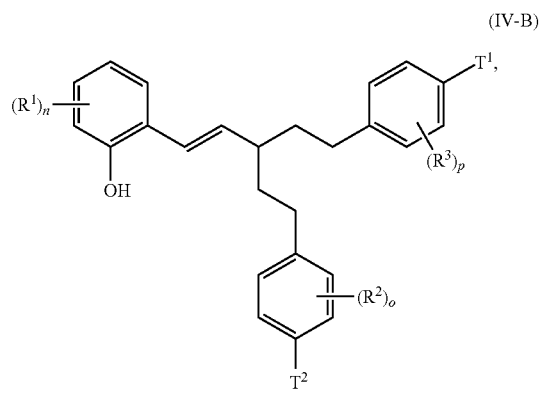

(IV-B)

in which $R^1$, $R^2$, $R^3$, n, o, p, $T^1$ and $T^2$ each have the meanings given above, and these are then coupled in an inert solvent in the presence of a base with a compound of the formula (V)

A-D-Q     (V), in which A and D have the meanings given in claim 1 and

Q represents a leaving group, such as, for example, halogen, tosylate or mesylate, to give compounds of the formula (IV-C)

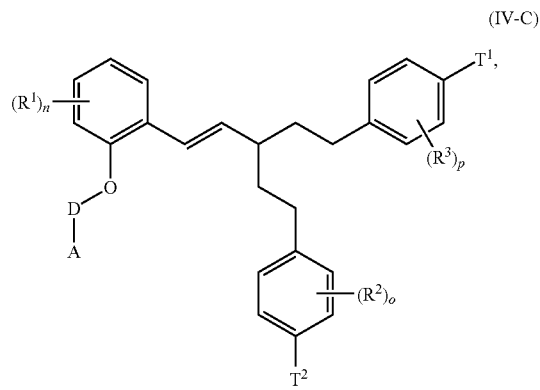

(IV-C)

in which A, D, $R^1$, $R^2$, $R^3$, n, o, p, $T^1$ and $T^2$ each have the meanings given above, and the resulting compounds of the formula (IV-A) or (IV-C) are then converted by hydrolysis of the ester groups $T^1$ and $T^2$ into the dicarboxylic acids of the formula (I), and the compounds of the formula (I) are separated where appropriate by methods known to the skilled person into their enantiomers and/or diastereomers, and/or where appropriate reacted with the appropriate (i) solvents and/or (ii) bases or acids to give the salts thereof.

5. A pharmaceutical composition comprising a compound as defined in claim 1 in combination with an inert, non-toxic, pharmaceutically suitable excipient.

6. The pharmaceutical composition of claim 5 further comprising one or more further active ingredients selected from the group consisting of organic nitrates, NO donors, cGMP-PDE inhibitors, stimulators of guanylate cyclase, agents having antithrombotic activity, agents lowering blood pressure, and agents altering lipid metabolism.

7. The pharmaceutical composition as claimed in claim 5 for the treatment and/or prevention of heart failure, angina pectoris, hypertension, pulmonary hypertension, ischemias, vascular disorders, thromboembolic disorders and arteriosclerosis.

8. A method for the treatment of heart failure, angina pectoris, hypertension, pulmonary hypertension, ischemias, vascular disorders, thromboembolic disorders and arteriosclerosis in humans and animals by administration of an effective amount of at least one compound as defined in claim 1.

9. A method for the treatment of heart failure, angina pectoris, hypertension, pulmonary hypertension, ischemias, vascular disorders, thromboembolic disorders and arteriosclerosis in humans and animals by administration of an effective amount of a pharmaceutical composition of claim 5.

\* \* \* \* \*